United States Patent [19]

Folkers et al.

[11] Patent Number: 4,550,109
[45] Date of Patent: Oct. 29, 1985

[54] LIPOIDAL BIOPTERIN COMPOUNDS

[75] Inventors: Karl Folkers; Klaus P. Laesecke, both of Austin, Tex.

[73] Assignee: The Board of Regents, The University of Texas System, Austin, Tex.

[21] Appl. No.: 615,812

[22] Filed: May 31, 1984

[51] Int. Cl.[4] .................................... C07D 241/00
[52] U.S. Cl. .................................................. 514/249
[58] Field of Search .................. 544/258, 261; 424/251

[56] References Cited

U.S. PATENT DOCUMENTS 4,371,514  2/1983  Nagatsu et al. ..................... 544/258

FOREIGN PATENT DOCUMENTS 79574   5/1983  European Pat. Off. ............ 544/258
57-4990 1/1982  Japan .

OTHER PUBLICATIONS

Schaub, J. et al., (*Archives of Disease in Childhood*, 1978, 53, 674–683).
*Helvetica Chimica Acta*—vol. 62, Fasc. 8(1979)—Nr. 264 264, Uber Pterinchemie 72, Mitteilung[1]) Trennung der Diastereomeren (6R)–und (6S)-5,6,7,8-Tetrahydro-1-Biopterin von Hans–Jurg Furrer, et al.
Matalon et al. (*Annals of Clinical and Laboratory Sc.*) vol. 12, No. 5, 411–414.
Niederwieser et al. (Eur. J. Pediatr., 138, 110–112) Original Investigations Atypical Phenylketonuria with Defective Biopterin Metabolism, Monotherapy with Tetrahydrobiopterin or Sepiapterin, Screening and Study of Biosynthesis in Man.
Kaufman et al. (*Pediatrics, vol. 70, No. 3, Sep. 1982* 376–380) Use of Tetrahydropterins in the Treatment of Hyperphenylalaninemia due to Defective Synthesis of Tetrahydrobiopterin.
Curtius et al. (*J. Neural Transmission, vol. 55*, 301–308) Short Communications Tetrahydrobiopterin: Efficacy in Endogenous Depression and Parkinson's Disease.
Niederwieser et al. (*Eur. J. Pediatr.*(1982) 138, Hyperphenylalaninemia with Neopterin Deficiency—A New Enzyme Defect Presumably of GTP Cyclohydrolase.
Leeming, et al. (*Biochemical Medicine 30, 328–332*(1983)) Intestinal Absorption of Tetrahydrobiopterin and Biopterin in man.
Bech, et al. (Acta Paediatr Scand. 72:449–454, 1983 Diagnostic and Therapeutic Aspects of Dihydrobiopterin Deficiency.

Curtius, et al. (*Lancet,* Mar. 19, 1983) 657–658 Serological and Biochemical Data.
Kaufman, et al. (*Annals of Neurology* vol. 14, No. 3, Sep. 1983 308–315) Tetrahydropterin Therapy for Hyperphenylalaninemia caused by Defective Synthesis of Tetrahydrobiopterin.
Kuster et al. (*J. Chromatog., 278, 245–254*) Gas Chromatog. Mass Spectrometry of Trimethylsilyl Pteridines.
*Chemical Abstract* 99:175478H 1′,2′-Diacyl-(6R,-S)-5,6,7,8-Tetrahydro-1-Biopterin (1983).
Niederwieser et al. (*Eur. J. Pediatr.,* 141, 208–214) GTP Cyclohydrolase I Deficiency, a new Enzyme Defect causing Hyperphenylalaninemia with Neopterin, Biopterin, Dopamine, and Serotonin Deficiencies and Muscular Hypotonia.
*Science vol. 219, Jan. 7, 1983* Effects of Tryosine Administration on Serum Biopterin in Normal Controls and Patients with Parkinson's Disease.

*Primary Examiner*—Veronica P. Hoke
*Attorney, Agent, or Firm*—Arnold, White & Durkee

[57] ABSTRACT

The present invention provides lipoidal biopterin and tetrahydrobiopterin compounds of the general structure:

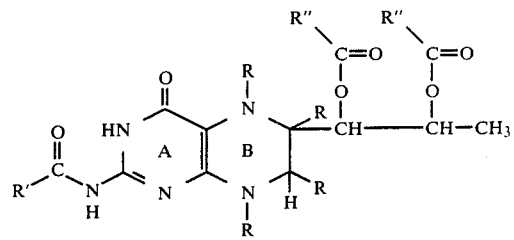

wherein
—R is absent when ring B has two double bonds,
—R is hydrogen when the two double bonds in ring B are absent, and
—R' and R" are selected from saturated or unsaturated, cyclic or non-cyclic hydrocarbons of 1 to 31 carbon units.

The compounds provided by this invention are oil soluble and can readily be formulated as an oil based pharmaceutical useful for the treatment of phenylketonuria, Parkinsonism, depression, senile dementia, Alzheimer's disease and related biopterin deficiency diseases.

7 Claims, No Drawings

LIPOIDAL BIOPTERIN COMPOUNDS

BACKGROUND OF THE INVENTION

This invention concerns biochemical, biomedical and clinical studies involving the administration of tetrahydrobiopterin to patients with diverse disease states and symptoms including phenylketonuria, Parkinsonism, endogenous depression, senile dementia, Alzheimer's disease, etc. Literature since 1978 which is relevant to this invention is summarized in this section on BACKGROUND.

1978

Schaub et al. (*Archives of Disease in Childhood*, 53, 674–683) administered tetrahydrobiopterin to a patient with atypical phenylketornuria (defective dihydrobiopterin synthesis) which had been detected at six months of age. After iv. administration of 2.5 mg/kg of chemically pure tetrahydrobiopterin hydrochloride, serum phenylalanine decreased from 20.4 to 2.1 mg/100 ml within three hours. Administration of 25 mg of tetrahydrobiopterin ($BH_4$) and 100 mg of ascorbic acid through a gastric tube decreased the serum phenylalanine from 13.7 to less than 1.6 mg/100 ml within three hours, and the level remained less than 2 mg/100 ml for two days.

1982

Matalon et al. (Annals of Clinical and Laboratory Science, 12, No. 5, 411–414) advanced the knowledge on the screening of the newborn for phenylketonuria (PKU), and differentiated the syndromes related to PKU. In classical PKU, phenylalanine hydroxylase is the deficient enzyme. In the atypical forms of PKU, the deficiency is in the enzymes affecting the production of tetrahydrobiopterin. Two types of atypical forms of PKU are known. One is caused by a deficiency of dihydropteridine reductase, and the other is caused by defects in the synthetic pathways of biopterin, termed as "biopterin synthesis deficiency". Analysis of oxidized pterins in urine by high performance liquid chromatography identifies classical PKU, dihydropteridine reductase deficiency, and biopterin synthetase defects. It was believed that the early recognition of these cofactor defects is essential for successful therapy, particularly with the atypical forms.

Niederwieser et al. (*Eur. J. Pediatr.* 138, 110–112) administered a single dose of tetrahydrobiopterin dihydrochloride, 10–20 mg/kg orally, to a patient with dihydrobiopterin deficiency, and observed the disappearance of clinical symptoms for four days, normalization of urinary phenylalanine, and serotonin, decrease of elevated neopterin for 2–3 days. A dose-dependent stimulation of serotonin production was observed. A similar effect was noted with even lower doses of L-sepiapterin. This patient was then treated with tetrahydrobiopterin dihydrochloride, 2.5 mg/kg daily. The patient, a girl of five years, was treated orally with 400 mg of $BH_4$ diHCL or 22 mg/kg. Within 3–4 hrs all symptoms disappeared, and the effect lasted for four days. Then, the symptoms reappeared and were again removed by $BH_4$. A single dose of 200 mg of $BH_4 2HCl$ or even only 50 mg of L-sepiapterin (2.5 mg/kg) both had practically the same long-lasting effect.

Kaufman et al. (Pediatrics, 70, No. 3, 376-380) administered $BH_4$ in the treatment of hyperphenylalaninemia due to defective synthesis of tetrahydrobiopterin and reported evidence that peripherally administered tetrahydropterins entered the brain. They administered 20 mg/kg/day orally for three days $BH_4$ to a male patient, 10 years old, divided doses were given every 12 hours. This administration increased cerebro spinal fluid biopterin concentrations of 20-fold, 2.5 hours after $BH_4$ had been given.

Hase et al. (*J. Inher. Metab. Dis.*, 5, 81–82) studied a case of tetrahydrobiopterin deficiency due to a defective synthesis of dihydrobiopterin. The dosage of $BH_4$ was 2.5 mg/kg. L-Sepiapterin was also administered at a level of 2.0 mg/kg. Both preparations were administered as oral loading tests and reduced serum phenylalanine concentrations markedly. The response to sepiapterin seemed to be less than $BH_4$ loading.

Narabayashi et al. (*Proc. Japan Acad.*, 58, Serv. B, 283–287) administered tetrahydrobiopterin to patients with Parkinsonian symptoms. There were five cases of idiopathic Parkinsonism. 400 mg of $BH_4$ was administered with 1600 mg of ascorbic acid. The improvement of akinesia and ADL was remarkable, although tremor and slight rigidity were not adequate influenced. The improvement continued for about two hours and then gradually diminished. No case presented dramatic improvement, but in all five cases improvement was moderate and mild. The symptoms of hypokinesia or akinesia were best benefitted. These were "single shot" oral administrations of $BH_4$ to five cases of Parkinsonism. The dosage range was 300 to 600 mg $BH_4$.

Curtius et al. (*Biochemical and Clinical Aspects of Pteridines*, Vol. 1, Walter de Gruyter & Co., Berlin, N.Y., 285–292) conducted therapeutic trials with tetrahydrobiopterin with three patients having endogenous depression and two patients with Parkinson's disease. They administered single oral doses of 0.9–1.0 g. In two patients with depression and both patients with parkinsonism, the main clinical symptoms improved or even disappeared between four and six hours after treatment.

Curtius et al. (*J. Neural Transmission*, 55, 301–308) again reported administration of tetrahydrobiopterin to one patient with agitation, two patients with inhibited endogenous depression and two patients with Parkinson's disease. Treatment was by single oral dosage of 0.9–1.0 g. Part of the clinical symptoms disappeared in the two patients with inhibited endogenous depression after 4–5 hours, and the symptoms reappeared approximately ten hours after the loading. Both patients with Parkinson's disease lost their hypokinesia and rigidity and part of the tremor four hours after $BH_4$ for a period of approximately five hours.

Leupold et al. (*Biochemical and Clinical Aspects of Pteridines*, Vol. 1, Walter de Gruyter & Co., New York, 307–317) studied tetrahydrobiopterin monotherapy in two siblings with dihydrobiopterin deficiency. They concluded that they have successfully treated two children suffering from dihydrobiopterin deficiency. The dosage for one case was 400 mg/kg/day or 22 mg/kg and then 200 mg/day or 11 mg/kg. The dosage for a second case was 10 mg/kg and then 200 mg/day or 11 mg/kg. The dosage for a second case was 10 mg/kg. There was a completed and prompt clinical recovery of one patient 3–4 hours after $BH_4$ administrration, strongly suggesting endogenous neuotransmitter production.

Niederwieser et al. (*Eur. J. Pediatr.*, 138, 97) reported a new enzyme defect involved in hyperphenylalaninemia. The symptoms were observed in a girl of four years with severe retardation in development, no head control, severe hypotonia and frequent episodes of hyperthermia without infection, and convulsion. Administration of $BH_4$ was at the level of 7.5 mg/kg orally. Plasma phenylalanine decreased within 4 and 8 hours.

1983

Leeming et al. (*Biochemical Medicine*, 30, 328–332) studied the intestinal absorption of tetrahydrobiopterin and biopterin in man. Doses in $BH_4$ were 10 mg and biopterin were 5 mg, which in some cases were combined with 200 mg of ascorbic acid. Only patients who had no history of malabsorption were included in the series. The results indicated that $BH_4$ and its oxidation product 7,8-dihydrobioptrin are slowly transported across the gut in man. 7,8-Dihydrobiopterin is reduced to $BH_4$ by a reductase substantially faster than is folic acid. Thus, in man after large oral doses of $BH_4$, some $BH_4$ may become available to function in the cell as a coenzyme.

Beck et al. (*Acta Paediatr. Scand.*, 72, 449–454) reported on the diagnostic and therapeutic aspects of dihydrobiopterin deficiency. A child at the age of 5½ months presented severe neurological symptoms. The treatment with $BH_4$ was an oral loading test with 40 mg of $BH_4$-dihydrochloride—"which has been maintained from the age of 6 months". Four hours after the first single dose of 40 mg of $BH_4$ given orally, serum phenylalanine decreased and 8 hours after this level was normal, and the effect lasted 48 hours. Then the level of phenylalanine increased. The next dose of 20 mg of $BH_4$ did not have an effect but another dose of 40 mg did cause a decrease of the amino acid to a normal level. Since the neurological symptoms had not disappeared completely, two large doses of 150 and 140 mg were given.

Aziz et al. (*J. Neurol., Neurosurgery, Psychiatry*, 46, 410–413) reported on the tetrahydrobiopterin metabolism in senile dementia of Alzheimer type. The patients studied were from acute medical wards, who had been admitted on account of one or more of the following illnesses: acute cerebrovascular disease, severe congestive cardiac failure, septicaemia, Huntington's disease, etc. The patients were divided into two groups. One group consisted of patients suffering from chronic mental confusion. The other group consisted of patients without mental symptoms. Tetrahydrobiopterin metabolism was shown to be disturbed in 18 patients with senile dementia of Alzheimer type.

Curtius et al. (Lancet, 657–658, Mar. 19, 1983) published a communication on the successful treatment of depression with tetrahydrobiopterin. A 53-year old female who had not responded to a wide variety of antidepressive drugs during 10 years of hospital care was given a dose of 1 g of $BH_4$ by mouth in the early morning for 3 days. This treatment induced intermittent vomiting although not as severe as that caused earlier by 5-hydroxytryptophan. On day 3, her mood had improved much and the improvement persisted for 3 days after $BH_4$ therapy stopped, but then this patient deteriorated. The biochemical measurements indicated no correlation between mood and urinary free dopamine or serotonin. For two months after this first trial, the patient was given no antidepressive drugs. Then, $BH_4$, 1 g daily was tried. After 5 days with no response, her diet was supplemented with tryptophan and tyrosine, nausea and vomiting had been restricting her intake of these amino acids. On day 6, there was a marked clinical improvement that lasted over a week. $BH_4$ therapy was continued with tryptophan, but the $BH_4$ dose was lowered to 500 mg daily on day 8, and to 200 mg daily on day 13 in search for an effective maintenance dose. When the patient was on 100 mg $BH_4$ daily, her mood gradually deteriorated. It was concluded that the use of $BH_4$ both alone and in combination with these amino acids should be considered a novel approach to antidepressive therapy.

Yamaguchi et al. (including Narabayashi (*Science*, 219, 75–77) reported on the effects of tyrosine administration on serum biopterin in normal controls and patients with Parkinson's disease. After oral administration of tyrosine, the increase in serum biopterin concentration was smaller in patients with Parkinson's disease (less than two-fold) than in healthy controls (three-to-seven-fold). These results suggested that tyrosine may have a regulatory role in biopterin biosynthesis and that patients with Parkinson's disease may have some abnormality in the regulation of biopterin biosynthesis.

Kaufman et al. (*Annals of Neurology*, 14, 308–315) reported on clinical treatment with 6-methyltetrahydropterin. The daily dose level was 8 mg/kg. There was an improvement of the patient's neurological symptoms including a pronounced decrease in eye rolling and drooling and a marked increase in muscle strength, coordination and physical activity.

Kuster et al. (*J. Chromatog.*, 278, 245–254) described data on gas chromatography-mass spectrometry to trimethylsilyl pteridines. The administration of pteridines to treat patients was not investigated.

Leeming et al. (*Biochem. Medicine*, 30, 328–332) measured the intestinal absorption of tetrahydrobiopterin and biopterin in man. The serum biopterin level following 10 mg tetrahydrobiopterin was not substantially altered by concurrent ascorbic acid. They found that the rate of intestinal absorption of biopterin in man is greater than that of tetrahydrobiopterin. This result was in agreement with earlier whole body studies in the rat when it was found that 90% of an oral dose of biopterin was absorbed and retained in comparison with only 10% of an oral dose of tetrahydrobiopterin.

1984

Niederwieser et al. (*Eur. J. Pediatr.*, 141, 208–214) reported on the guanosintriosphate-cyclohydrolase I deficiency, a new enzyme defect causing hyperphenylalaninemia hypotonia. A 4-year old patient with elevated phenylalanine, severe retardation in development, and severe muscular abnormalities, and convulsions was orally treated with L-erythro-tetrahydrobiopterin. A single dose of 7.5 mg/kg of $BH_4$-dihydrochloride was administered, and this patient was treated with other drugs. Subsequently, this patient was treated only with $BH_4$ and the dose in this sequence was increased from 3 mg/kg per day which was used in conjunction with other drugs to a higher dose of 5 mg/kg/day of $BH_4$ when it was used along. Under this $BH_4$ monotherapy, the muscle tone improved considerably and the child had good head control and was able to sit with support and to laugh.

Curtius et al. (*Advances in Neurology*, 40, Ed. R. G. Hassler & J. F. Christ, Raven Press, N.Y., 463–466) have again reported on the therapeutic efficacy of tetrahydrobiopterin in Parkinson's disease. He noted that large scale clinical testing of $BH_4$ has posed difficulties, one of which is that pure BH₄ has only recently become available and that the compound is expensive. In this study, he and his associates administered BH₄ to two patients with Parkinson's disease, and although the results are preliminary, the results indicate that this may be a useful form of therapy in certain cases of Parkinson's disease. They administered a single 1 gram dose level of BH₄ to two Parkinsonian patients. Between 4 and 5 hours after treatment, the symptoms of hypokinesia and rigidity disappeared completely in both patients, but tremor was only particularly improved. The benficial effect of BH₄ lasted approximately 5 hours at which time the prior clinical symptoms reappeared. The 1 gram of BH₄ was mixed with 100 mg of ascorbic acid in water and given orally one hour before breakfast. These two patients were observed over the course of the day for signs of clinical improvement and symptoms were scored. The scoring showed an improvement in hypokinesia, tremor, rigidity and elevation of mood.

THE FAILURE OF THERAPY WITH TETRAHYDROBIOPTERIN

According to the literature of the BACKGROUND, many researchers questioned whether tetrahydrobiopterin penetrated the blood brain barrier of man to make possible an enhancement of natural biochemical mechanisms which are basic to the disease states of Parkinsonism, etc. Apparently, some investigators believed that tetrahydrobiopterin did not cross the blood brain barrier at all, but other investigators, Kaufman, et al. in 1982 (*Pediatrics,* 70, No. 3, 376–380) reported evidence that peripherally administered tetrahydrobiopterin does enter the brain, in principle, if not at a therapeutically effective level.

The question is not whether there is zero entrance of tetrahydrobiopterin into the brain, but whether the crossing of the blood brain barrier by tetrahydrobiopterin is great enough under practical conditions of therapy to allow a meaningful improvement in the biochemical mechanisms of the brain which, in turn, is reflected by a lessening of a disease. Curtius et al. in 1984 (*Advances in Neurology,* 40, Ed. R. G. Hassler & J. F. Christ, Raven Press, N.Y., 463–466) updated this failure of tetrahydrobiopterin to cross effectively this blood brain barrier by his statement (pg. 466) that—"it is possible that more lipophilic, active hydroxylase cofactors may achieve higher brain cofactor concentrations for a longer period of time, which would enhance the effectiveness of cofactor administration in Parkinson's disease. We are currently investigating the ability of synthetic and active cofactor analogs to penetrate the blood brain barrier. It is hoped that this approach may ultimately be more effective than BH₄ administration for the treatment of Parkinson's disease and other diseases involving deficits of biogenic amine neurotransmitters".

We recognized that an appropriately designed and synthesized derivative of tetrahydrobiopterin can be superior to tetrahydrobiopterin in crossing the blood brain barrier and allow an effective therapy of disease states which appear related to tissue deficiencies of tetrahydrobiopterin. Such derivatives can also be superior for formulation and stability.

SUMMARY OF THE INVENTION

Tetrahydrobiopterin has very low solubility in water and no solubility in lipoidal systems. The dihydrochloride of tetrahydrobiopterin does have a certain water solubility, but formulations of the dihydrochloride may have sufficiently low pH levels which can cause them to be unsatisfactory for certain therapeutic uses. Acidic solutions can be irritating. The relatively ineffective therapeutic administration of tetrahydrobiopterin dihydrochloride to patients implies an inadequate crossing of the blood brain barrier by tetrahydrobiopterin in a physiological environment.

A therapeutically successful derivative of tetrahydrobiopterin must be non-toxic and capable of metabolically yielding tetrahydrobiopterin after administration or yielding a modified form of tetrahydrobiopterin in which the coenzymatic functionality is unchanged.

Such a needed derivative of tetrahydrobiopterin could be considered as a "pro-drug" which, on administration to a human subject, is either converted to tetrahydrobiopterin or a modified tetrahydrobiopterin with unchanged coenzymatic functionality.

It has now been discovered, in accordance with the present invention, that new 2-N-acyl-1',2'-di-O-acyl-L-biopterins and 2-N-acyl-1',2'-di-O-acyl-L-tetrahydrobiopterins can be synthesized, and in large quantity, and at relatively low cost, and which have chemical features which make them superior to tetrahydrobiopterin.

In accordance with the present invention, the lipoidal biopterins and tetrahydrobiopterins are represented by the following structure:

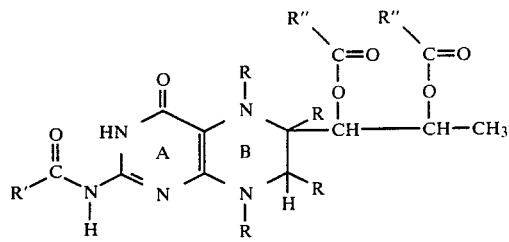

wherein
— R is absent when there are two double bonds in ring B;
— R is hydrogen when the two double bonds in ring B are absent; and
— R' and R" are independently saturated or unsaturated, aliphatic hydrocarbon groups which are balanced in molecular weight such that they confer to the lipoidal compound a lipoidal property.

Generally R' and R" are selected from hydrocarbons having from 1 to 31 carbon units, with the limitation that the sum of carbon units of R'+2R" is greater than 10 but less than 33.

In these derivatives, the 2-N-acyl group is desirably from 9 to 32 and preferably 9 to 20 carbon units so as to confer lipoidal characteristics upon the final product. The 2-N-acyl group is exemplified by decanolyl-, palmitoyl-, stearoyl- and linoleyl. The 2-N-acyl group may be saturated as is stearoyl-or unsaturated as is linoleyl. In addition, non-toxic aromatic 2-N-acyl groups like phenylacetyl can also confer the desirable lipoidal characteristics to the final product. The 1',2'-di-O-acyl groups, are desirably lower molecular weight alkyls and alkenyls having from 2 to 8 and preferably 2 to 4 carbon units, with acetyl being exemplary.

DETAILED DESCRIPTIONS OF PREFERRED EMBODIMENTS

Clinical Formulation of Derivatives

The derivatives of this invention, such as 2-N-stearoyl-1′,2′-di-O-acetyl-L-biopterin and L-tetrahydrobiopterin are readily soluble in pharmaceutically effective carriers such as vegetable oils (e.g., corn oil, soybean oil or peanut oil, etc.) and at a concentration suitable for the preparation of sealed soft gelatin capsules containing a formulation of the derivative in the vegetable oil, and which completely fills the capsule and in the absence of an air bubble which would contain oxygen. Such a completely filled soft gelatin capsule containing the derivative in the vegetable oil is stable and very suitable for all clinical use. Heretofore, it has not been possible to formulate tetrahydrobiopterin or biopterin in a vegetable oil because of the insolubility of these substances in such oil.

Synthesis of Useful Lipophilic Forms of Biopterin

In order to achieve lipophilic forms of biopterin and tetrahydrobiopterin, derivatives of 1′,2′-Di-O-acetyl-biopterin, I, with the general formula, II, were synthesized.

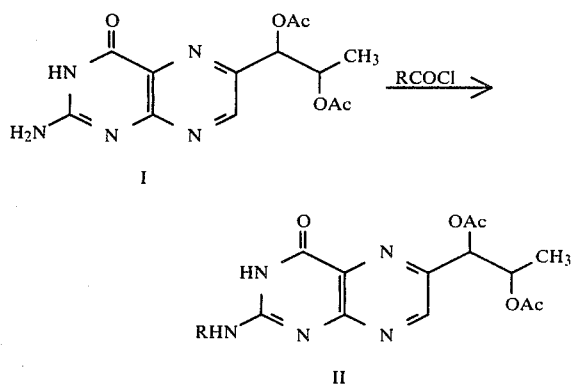

R = fatty acid
Ac = COCH$_3$

R consists of naturally occurring fatty acids, which can be saturated or unsaturated.

EXAMPLES

2N-Acetyl-1′,2′-di-O-Acetyl-L-Biopterin

This substance was synthesized according to the procedure of Furrer et al. (H. J. Furrer, J. H. Bieri, M. Viscontini; *Helv. Chim. Acta*, 62, 2577 (1979)). Thus, a suspension of L-biopterin was allowed to react with acetic anhydride and acetic acid to form the triacetyl-L-biopterin in 100% yield as a light yellow powder.

1′,2′-Di-O-Acetyl-Biopterin 1.0 g of 2-N-Acetyl-1′,2′-di-O-acetyl-L-biopterin was added to 80 ml of methanol in the dark and the mixture was heated under reflux and under exclusion of moisture for 36 hrs. The mixture (a part of the product had separated) was cooled to room temperature, the precipitate was removed by filtration and dried under vacuum to yield 680 mg (76%) of 1′,2′-di-O-acetyl-biopterin.

The synthesis of this diacetylbiopterin is also described in the literature by Kappel (M. Kappel; *Thesis,* Univ. of Konstanz 1981) and mentioned by Viscontini (M. Viscontini, C.A. 99, 1754786.).

General procedure for the synthesis of 2-N-Acyl-1′,2′-di-O-acetyl-L-biopterins 450 mg (1.38 mmol) 1′,2′-Di-O-acetyl-L-biopterin (H. J. Furrer, J. H. Bieri, M. Viscontini; *Helv. Chim. Acta* 62, 2577 (1979)); M. Kappel, Dissertation, Univ. of Konstanz, W.G., 1981) was suspended in 20 ml dry pyridine and then 2.7 mmol fatty acid chloride, such as stearoylchloride, was added dropwise. The mixture was stirred under exclusion of moisture at room temperature. The course of the reaction was monitored by TLC with ethylacetate as an eluent. After 16 hrs., another 2.7 mmol of the fatty acid choride, such as stearoylchloride was added. After 20 hrs, the clear and yellow solution was evaporated under diminished pressure (40° C. bath temperature) finally together with toluene, and the residue was then chromotographed on a silica gel column with ethylacetate/toluene=3/1. After evaporation of the solvents, the product was obtained as a clear colorless oil or by crystallization from ethanol.

Four new products were obtained by this method, and are in Table 1. The chain length of the group R from acid ranged from C$_{10}$ to C$_{18}$ units, as examples. Two double bonds in an R group from a fatty acid were introduced by the synthesis of a linoleyl-derivative.

TABLE I

| New Products from 1′,2′-Di-O—acetyl-L-biopterin | RF-values | | Melting Point |
|---|---|---|---|
| | (a) | (b) | |
| 2-N—Decanoyl-1′,2′-di-O—acetyl-L-biopterin | 0.50 | 0.20 | oil |
| 2-N—Palmitoyl-1′,2′-di-O—acetyl-L-biopterin | 0.69 | 0.31 | 57° C. |
| 2-N—Stearoyl-1′,2′-di-O—acetyl-L-biopterin | 0.71 | 0.35 | 82° C. |
| 2-N—Linoleyl-1′,2′-di-O—acetyl-L-biopterin | 0.69 | 0.31 | oil |
| 2-N—Phenylacetyl-1′,2′-di-O—acetyl-L-biopterin | 0.76 | 0.63 | oil | a = ethylacetate;
b = toluene/ethylacetate = 1/1

The Rf-value was detected by absorption of the product at 254 mm after TLC development on silica gel.

The lipophilicity increases with the increasing chain length, which can be seen easily by the higher Rf-values for the products with the larger chains.

ANALYTICAL DATA

Additional analytical data ($^1$H-NMR) for 2-N-stearoyl-1′,2′-di-O-acetyl-L-biopterin are:

$^1$H-NMR(200 MHz, CDCl$_3$): 1.2–1.5 ppm (bs, —CH$_2$ from fatty acid and CH$_3$)
2.0 ppm (s, C-2′-Oac) 2.19 ppm (s, C-1′-OAc), 5.48 ppm (m, C-2′H) 6.05 ppm
(d, c-1′H), 8.9 ppm, (bs, N-3-H).

MASS SPECTRUM FOR 2-N-STEAROYL-1′,2′-DI-O-ACETYL-L-BIOPTERIN

M/E 587: molecular peak (mol.p.)
M/E 544: mol.p—COCH$_3$
M/E 527: mol.p.—ACOH
M/E 501: mol.p.—2COCH$_3$
M/E 485: mol.p.—COCH$_3$—OCOCH$_3$
M/E 469: mol.p.—2OAc
M/E 428: mol.p.

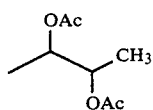

M/E 267: mol.p.—CH$_3$(CH$_2$)$_{16}$CO base peak 43: COCH$_3$

EXAMPLE OF STABILITY

In order to determine the stability of 2-N-Stearoyl-1',2'-di-O-acetyl-biopterin in solution 50 mg of the dry substance was dissolved in 10 ml of ethanol (95%). This homogenous solution was kept at room temperature. The amount of alcoholysis was determind by TLC-detection with ethylacetate as an eluent (silica gel, UV 254 nm). The reaction was followed by determining 1',2'-Di-O-acetyl-biopterin. The estimated degree of reaction after different times was as follows:

30 min.: no change
1 hour: trace of reaction
5 hours: 10% reaction
24 hours: 20% reaction
1 week: 50% reaction This example clearly indicates that 2-N-stearoyl-1',2'-di-O-acetyl-biopterin has a 2-N acyl group which is sensitive to hydrolysis and alcoholysis under a great range of conditions. The sensitivity also clearly indicates a sensitivity for separation of the acyl group under physiological conditions in vitro and in vivo, and this sensitivity is desirable in an aspect of the invention described herein.

It is not preferred to formulate this new lipoidal product in an aqueous or alcoholic medium. Therefore, this new product was formulated with vegetable oil and the oil formulation placed in a sealed soft gelatin capsule in the absence of air. This new lipoidal product should be indefinitely stable in oil formulation. Homogenous solutions of 5 mg of 2-N-stearoyl-1',2'-di-O-acetyl-L-biopterin or 5 mg of 2-N-palmitoyl-1',2'-di-O-acetyl-L-biopterin on 0.3 ml of soybean oil (Scherer Corp.) remained unchanged for at least 4 weeks.

REDUCTION

The new products derived from biopterin were catalytically reduced with hydrogen. Reduction of the pyrazine ring occurred quantitatively.

REDUCTION OF N-STEAROYL-1',2'-DI-O-ACETYL-L-BIOPTERIN 50 mg (0.085 mmol) of N-Stearoyl-1',2'-di-O-acetyl-L-biopterin was dissolved in a mixture of 10 ml toluene, 5 ml of methanol and 5 ml ethylacetate. A three-necked flask was flushed with nitrogen and a catalytic amount ca. of palladium on charcoal (10%) was added. After flushing with hydrogen, the mixture was stirred for 16 hrs. filtered under an inert atmosphere, and evaporated by means of a rotary evaporator at room temperature. Thus, a fine white powder was obtained. Rf. 0.50 (ethylacetate, silica gel)

$^1$H-NMR-DATA FOR 21 -N-STEAROYL-1',2'-DI-O-ACETYL-TETRAHYDROBIOPTERIN

δ(ppm), DMSO-d$^6$; 3.3–3.1 (m, H-C(6) and 2H-C(7)), 2.25–2.1 (m, acetylprotons), 1.35 (s, stearoylprotons).

These 2-N-acyl-1',2'-di-O-acyl-tetrahydrobiopterins, 2-N-acyl-1',2'-di-O-acyl-biopterins of this invention, and particularly 2-N-stearoyl-1',2'-di-O-acetyl-biopterin, are useful. This usefulness is multiple, because these new products are metabolically reducible and can be directly used to treat Parkinson's disease and other illness, and because they have a lipoidal nature in great contrast to biopterin and tetrahydrobiopterin. The lipoidal nature means these new products are soluble in vegetable oils in contrast to the insolubility in oils of biopterin and tetrahydrobiopterin. These products are useful in oil-formulation for encapsulation in sealed soft gelatin capsules in the absence of air, and for administration of such capsules to human subjects with disease. These products in the biopterin structural form and in the tetrahydrobiopterin structural form are clinically useful for administration of patients having parkinson's disease, behavioral disease, etc.

Our examples illustrate synthesis of new 2-N-acyl-1',2'-di-O-acetyl-biopterins and 2-N-acyl-1',2'-di-O-acetyl-5,6,7,8-tetrahydrobiopterins and particularly the products with a saturated aliphatic acyl group, such as stearoyl, which is not subject to oxidation. These examples, are represented and not restrictive. Several aspects of the new lipoidal products are inventive; the 2-N-acyl group is relatively labile and can be metabolically removed with greater ease than removal of the acetyl groups. These relative stabilities allow the new products to be coenzymatic and to penetrate usefully the blood brain barrier for effective therapy. The lipoidal characteristics is also useful and inventive and may be achieved with an N-acyl group of less than 10 carbon atoms and more than 18 carbon atoms. Moreover, one or more double bonds may be in the acyl group as there are 2 double bonds in linoleyl-. Additionally, the replacement of acetyl groups with the 3-carbon side chain of propionyl or other groups which serve the same purpose as acetyl are also representative and not restrictive. Furthermore, such lipoidal products having usefulness may also be achieved by diminishing the size of the 2-N-acyl group and replacing the acetyl groups by other groups of higher molecular weight.

The foregoing description has been directed to particular embodiments of the invention in accordance with the requirements of the Patent Statutes for purposes of illustration and explanation. It will be apparent, however, to those skilled in the art that many modifications and changes will be possible without departing from the spirit and scope of the invention. It is intended that the following claims be interpreted to embrace all such modifications and changes.

What is claimed is:

1. A lipoidal compound having the formula:

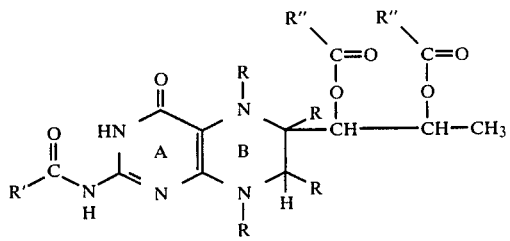

wherein
— R is absent when there are two double bonds in ring B;
— R is hydrogen when the two double bonds in ring B are absent; and —R' and R" are independently saturated or unsaturated, aliphatic hydrocarbon groups which are balanced in molecular weight such that they confer to the lipoidal compound a lipoidal property, and wherein —R' has 8 to 19 carbon units and —R" has 1 to 3 carbon units.

2. The compound of claim 1 which is 2-N-stearoyl-1',2'-di-O-acetyl-biopterin.

3. The compound of claim 1 which is 2-N-stearoyl-1',2'-di-O-acetyl-5,6,7,8,-tetrahydrobiopterin.

4. The compound of claim 1 which is
2-N-decanoyl-1',2'-di-O-acetyl-L-biopterin,
2-N-palmitoyl-1',2'-di-O-acetyl-L-biopterin, or
2-N-linoleyl-1',2'-di-O-acetyl-L-biopterin.

5. The compound of claim 1 which is
2-N-decanoyl-1',2'-di-O-acetyl-5,6,7,8,-tetraphydrobiopterin,
2-N-palmitoyl-1',2'-di-O-acetyl-5,6,7,8,-tetrahydrobiopterin, or
2-N-linoleyl-1',2'-di-O-acetyl-5,6,7,8,-tetrahydrobiopterin.

6. A pharmaceutical composition useful for treating brain-related biopterin deficiencies which comprises a pharmaceutically acceptable carrier and a pharmaceutically effective amount of a compound of claim 1.

7. A method of treating brain-related biopterin deficiencies which comprises administering to a patient in need of such treatment a pharmaceutically effective amount of a compound of claim 1.

* * * * *